(12) United States Patent
Pandit et al.

(10) Patent No.: US 11,963,488 B2
(45) Date of Patent: Apr. 23, 2024

(54) SYSTEM AND METHOD FOR ROOT ZONE SOIL MOISTURE ESTIMATION FOR VEGETATION COVER USING REMOTE SENSING

(71) Applicant: Tata Consultancy Services Limited, Mumbai (IN)

(72) Inventors: Ankur Pandit, Thane (IN); Jayantrao Mohite, Thane (IN); Suryakant Ashok Sawant, Thane (IN); Srinivasu Pappula, Hyderabad (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 371 days.

(21) Appl. No.: 17/646,731

(22) Filed: Jan. 3, 2022

(65) Prior Publication Data
US 2022/0312699 A1    Oct. 6, 2022

(30) Foreign Application Priority Data

Feb. 26, 2021   (IN) .............................. 202121008176

(51) Int. Cl.
*A01G 25/16*    (2006.01)
*G01N 33/24*    (2006.01)
(Continued)

(52) U.S. Cl.
CPC ......... *A01G 25/167* (2013.01); *G01N 33/246* (2013.01); *G01S 19/14* (2013.01); *G01S 19/256* (2013.01); *G01S 19/26* (2013.01)

(58) Field of Classification Search
CPC .... A01G 25/167; G01N 33/246; G01S 19/14; G01S 19/256; G01S 19/26
(Continued)

(56) References Cited

FOREIGN PATENT DOCUMENTS

CN    107389895 A   * 11/2017   .......... G01N 33/246
CN    107505265 A    12/2017
(Continued)

OTHER PUBLICATIONS

Chenyang Xu et al., "Monitoring Surface Soil Moisture Content over the Vegetated Area by Integrating Optical and SAR Satellite Observations in the Permafrost Region of Tibetan Plateau", Remote Sensing, Jan. 2020, vol. 12(1), MDPI, https://www.mdpi.com/2072-4292/12/1/183.
(Continued)

*Primary Examiner* — Harry K Liu
(74) *Attorney, Agent, or Firm* — FINNEGAN, HENDERSON, FARABOW, GARRETT & DUNNER LLP

(57) ABSTRACT

This disclosure relates generally to root zone moisture estimation for vegetation cover using remote sensing. Conventionally, it is challenging to estimate root zone soil moisture using only satellite data. Moreover, estimation of soil moisture under vegetation cover based on bare surface soil moisture and vegetation parameters is not available. The disclosed method and system facilitate estimation of an ensemble of soil moisture under vegetation cover and root zone soil moisture using process based soil water balance for spatial estimation of root zone soil moisture. The system estimates bare surface soil moisture for different soil types/textures using the baseline bare surface model and soil properties derived from satellite data and in-situ sensors. The method further provides temporal spatially distributed soil moisture inputs to an intelligent irrigation management/information system which is very important to reduce and regulate water consumption.

15 Claims, 6 Drawing Sheets

(51) Int. Cl.
*G01S 19/14* (2010.01)
*G01S 19/25* (2010.01)
*G01S 19/26* (2010.01)

(58) Field of Classification Search
USPC ......................................................... 342/352
See application file for complete search history.

(56) References Cited

FOREIGN PATENT DOCUMENTS

| CN | 108761034 A | * | 11/2018 | ........... G01N 33/246 |
| CN | 108802728 A | * | 11/2018 | ......... G01N 33/0098 |
| CN | 110795895 A | * | 2/2020 | |
| CN | 111239209 A | * | 6/2020 | ........... G01N 27/221 |
| CN | 112014542 A | * | 12/2020 | ............. G01N 21/47 |

OTHER PUBLICATIONS

Cheng-yong Wu et al., "Remotely sensed estimation and mapping of soil moisture by eliminating the effect of vegetation cover", Journal of Integrative Agriculture, Feb. 2019, vol. 18 (2) pp. 316-327, Research Gate, https://www.researchgate.net/publication/330858700_Remotely_sensed_estimation_and_mapping_of_soil_moisture_by_eliminating_the_effect_of_vegetation_cover/link/5d4cdd65299bf1995b70b5ee/download.

Nawa Raj Pradhan, "Estimating growing-season root zone soil moisture from vegetation index-based evapotranspiration fraction and soil properties in the Northwest Mountain region, USA", Hydrological Sciences Journal, May 2019, pp. 771-788, Tandf online, https://www.tandfonline.com/doi/pdf/10.1080/02626667.2019.1593417?needAccess=true.

Nabi Olah Gholami Bidkhani et al., "Influence of soil texture on the estimation of bare soil moisture content using MODIS images", Remote Sensing, Sep. 2018, pp. 911-920, Tandf online, https://www.tandfonline.com/doi/pdf/10.1080/22797254.2018.1514986?needAccess=true.

Zhongling Gao, A method of estimating soil moisture based on the linear decomposition of mixture pixels, Mathematical and Computer Modelling, Aug. 2013, vol. 53, Issue:3-4 pp. 606-613. Elsevier, https://reader.elsevier.com/reader/sd/pii/S0895717711006595?token=8B169A66C0077BAFEB43678D55970B45CB9EB1649F41F451439519DA2D56CE49A07F9736E5B1CC7AB0443D774565CA13&originRegion=eu-west-1&originCreation=20211221082715.

* cited by examiner

```
┌─────────────────────────────────────────────────┐
│ ESTIMATING BARE SURFACE SOIL MOISTURE ASSOCIATED│
│ WITH BARE SOIL IN A GEOGRAPHICAL AREA BY APPLYING│
│ A SOIL MOISTURE ESTIMATION MODEL TO A REMOTE    │── 302
│ SENSING DERIVED DATA, THE REMOTE SENSING DERIVED│
│ DATA OBTAINED UNDER NO-VEGETATION CONDITION IN  │
│ THE GEOGRAPHICAL AREA USING A REMOTE SENSING    │
│ TECHNIQUE                                       │
└─────────────────────────────────────────────────┘
                        ↓
┌─────────────────────────────────────────────────┐
│ ESTIMATING, AT A PLURALITY OF TIME-INSTANTS,    │
│ VEGETATION SURFACE SOIL MOISTURE ASSOCIATED WITH│
│ THE SOIL IN THE GEOGRAPHICAL AREA UNDER VEGETATION│
│ COVER ON THE SOIL, THE VEGETATION SURFACE SOIL  │
│ MOISTURE AT THE PLURALITY OF TIME INSTANTS      │
│ COMPUTED BASED ON THE BARE SOIL MOISTURE, A SOIL│── 304
│ PARAMETER, A WEATHER PARAMETER, A CROP          │
│ PARAMETER, ONE OR MORE TIME-SERIES SATELLITE    │
│ DERIVED REMOTE SENSING PARAMETERS, WHEREIN THE  │
│ ONE OR MORE TIME-SERIES SATELLITE DERIVED REMOTE│
│ SENSING PARAMETERS DERIVED BASED ON OPTICAL     │
│ SENSING DATA OBTAINED AT THE PLURALITY OF TIME  │
│ INSTANTS                                        │
└─────────────────────────────────────────────────┘
                        ↓
┌─────────────────────────────────────────────────┐
│ ESTIMATING A POINT-BASED ROOT ZONE SOIL MOISTURE│
│ USING A USING SOIL WATER BALANCE MODEL, WHEREIN │
│ THE SOIL WATER BALANCE MODEL COMPUTES ROOT ZONE │
│ WATER BALANCE ON A PERIODIC BASIS BASED ON WATER│
│ STORED IN THE ROOT ZONE AT PERIODIC INTERVALS, AND│── 306
│ PRECIPITATION, IRRIGATION, DRAINAGE AND         │
│ EVAPOTRANSPIRATION AMOUNT OF WATER DURING THE   │
│ PERIODIC INTERVALS                              │
└─────────────────────────────────────────────────┘
                        ↓
┌─────────────────────────────────────────────────┐
│ DETERMINING SPATIALLY DISTRIBUTED ROOT ZONE SOIL│
│ MOISTURE AT THE GEOGRAPHICAL LOCATION USING THE │
│ VEGETATION SURFACE SOIL MOISTURE AND POINT BASED│── 308
│ ROOT ZONE SOIL MOISTURE                         │
└─────────────────────────────────────────────────┘
```

FIG. 3   ← 300

SYSTEM AND METHOD FOR ROOT ZONE SOIL MOISTURE ESTIMATION FOR VEGETATION COVER USING REMOTE SENSING

PRIORITY CLAIMS

This US patent application claims priority under 35 U.S.C. § 119 to Indian Application No. 202121008176, filed on 26 Feb. 2021. The entire contents of the aforementioned application are incorporated herein by reference.

TECHNICAL FIELD

The disclosure herein generally relates to the field of precision farming, and, more particularly, to system and method for root zone soil moisture estimation for vegetation cover using remote sensing.

BACKGROUND

The spatio-temporal distribution of soil moisture has widespread importance in agriculture, climatology, hydrology, floods, meteorology, drought forecasting, and monitoring. Such spatio-temporal distribution also forms a crucial piece of knowledge required to model a variety of environmental processes. In the context of agriculture, several studies have been carried out where bare surface soil moisture was estimated using theoretical and/or empirical and/or semi-empirical models incorporating satellite remote sensing information. However, estimating soil moisture under agricultural vegetation in different growth stages is still a challenging task.

Low-frequency L-Band Synthetic Aperture Radar (SAR) satellite data is suitable for soil moisture estimation under agricultural vegetation. This is due to its higher penetration potential across dense vegetation as compared to the other available band such as C band and X band. Investigations on estimating soil moisture under vegetation have been carried out using L-band data but the problem is not yet solved satisfactorily. Presently, Advanced land Observing Satellite (ALOS-2) is the only active L-band SAR mission hosted by the Japan Aerospace Exploration Agency (JAXA™) In certain regions, for example, Indian region, ALOS-2 acquisition frequency is much lower, therefore, it is difficult to develop agriculture monitoring services using only this platform.

SUMMARY

Embodiments of the present disclosure present technological improvements as solutions to one or more of the above-mentioned technical problems recognized by the inventors in conventional systems.

For example, in one embodiment, a method for root zone soil moisture estimation under vegetation using remote sensing is provided. The method includes estimating bare surface soil moisture associated with bare soil in a geographical area by applying a soil moisture estimation model to a remote sensing derived data, via one or more hardware processors, the remote sensing derived data obtained under no-vegetation condition in the geographical area using a remote sensing technique. Further, the method includes estimating, at a plurality of time-instants, vegetation surface soil moisture associated with the soil in the geographical area under vegetation cover on the soil, via the one or more hardware processors, the vegetation surface soil moisture at the plurality of time instants computed based on the bare soil moisture, a soil parameter, a weather parameter, a crop parameter, one or more time-series satellite derived remote sensing parameters, wherein the one or more time-series satellite derived remote sensing parameters derived based on optical sensing data obtained at the plurality of time instants. Furthermore, the method includes estimating, via the one or more hardware processors, a point-based root zone soil moisture using a using soil water balance model, wherein the soil water balance model computes root zone water balance on a periodic basis based on water stored in the root zone at periodic intervals, and precipitation, irrigation, drainage and evapotranspiration amount of water during the periodic intervals. Also, the method includes determining, via the one or more hardware processors, spatially distributed root zone soil moisture at the geographical location using the vegetation surface soil moisture and point based root zone soil moisture.

In another aspect, a system for root zone soil moisture estimation under vegetation using remote sensing is provided. The system includes a memory storing instructions, one or more communication interfaces, and one or more hardware processors coupled to the memory via the one or more communication interfaces, wherein the one or more hardware processors are configured by the instructions to estimate bare surface soil moisture associated with bare soil in a geographical area by applying a soil moisture estimation model to a remote sensing derived data, the remote sensing derived data obtained under no-vegetation condition in the geographical area using a remote sensing technique. Further, the one or more hardware processors are configured by the instructions to estimate, at a plurality of time-instants, vegetation surface soil moisture associated with the soil in the geographical area under vegetation cover on the soil, the vegetation surface soil moisture at the plurality of time instants computed based on the bare soil moisture, a soil parameter, a weather parameter, a crop parameter, one or more time-series satellite derived remote sensing parameters, wherein the one or more time-series satellite derived remote sensing parameters derived based on optical sensing data obtained at the plurality of time instants. Furthermore, the one or more hardware processors are configured by the instructions to estimate a point-based root zone soil moisture using a using soil water balance model, wherein the soil water balance model computes root zone water balance on a periodic basis based on water stored in the root zone at periodic intervals, and precipitation, irrigation, drainage and evapotranspiration amount of water during the periodic intervals. Also, the one or more hardware processors are configured by the instructions to determine spatially distributed root zone soil moisture at the geographical location using the vegetation surface soil moisture and point based root zone soil moisture.

In yet another aspect, a non-transitory computer readable medium for a method for root zone soil moisture estimation under vegetation using remote sensing is provided. The method includes estimating bare surface soil moisture associated with bare soil in a geographical area by applying a soil moisture estimation model to a remote sensing derived data, via one or more hardware processors, the remote sensing derived data obtained under no-vegetation condition in the geographical area using a remote sensing technique. Further, the method includes estimating, at a plurality of time-instants, vegetation surface soil moisture associated with the soil in the geographical area under vegetation cover on the soil, via the one or more hardware processors, the vegetation surface soil moisture at the plurality of time instants computed based on the bare soil moisture, a soil parameter, a weather parameter, a crop parameter, one or more time-series satellite derived remote sensing parameters, wherein the one or more time-series satellite derived remote sensing parameters derived based on optical sensing data obtained at the plurality of time instants. Furthermore, the method includes estimating, via the one or more hardware processors, a point-based root zone soil moisture using a using soil water balance model, wherein the soil water balance model computes root zone water balance on a periodic basis based on water stored in the root zone at periodic intervals, and precipitation, irrigation, drainage and evapotranspiration amount of water during the periodic intervals. Also, the method includes determining, via the one or more hardware processors, spatially distributed root zone soil moisture at the geographical location using the vegetation surface soil moisture and point based root zone soil moisture.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3 is a process flow diagram of a method for root zone soil moisture estimation for vegetation cover using remote sensing according to some embodiments of the present disclosure.

DETAILED DESCRIPTION

Figure 1:
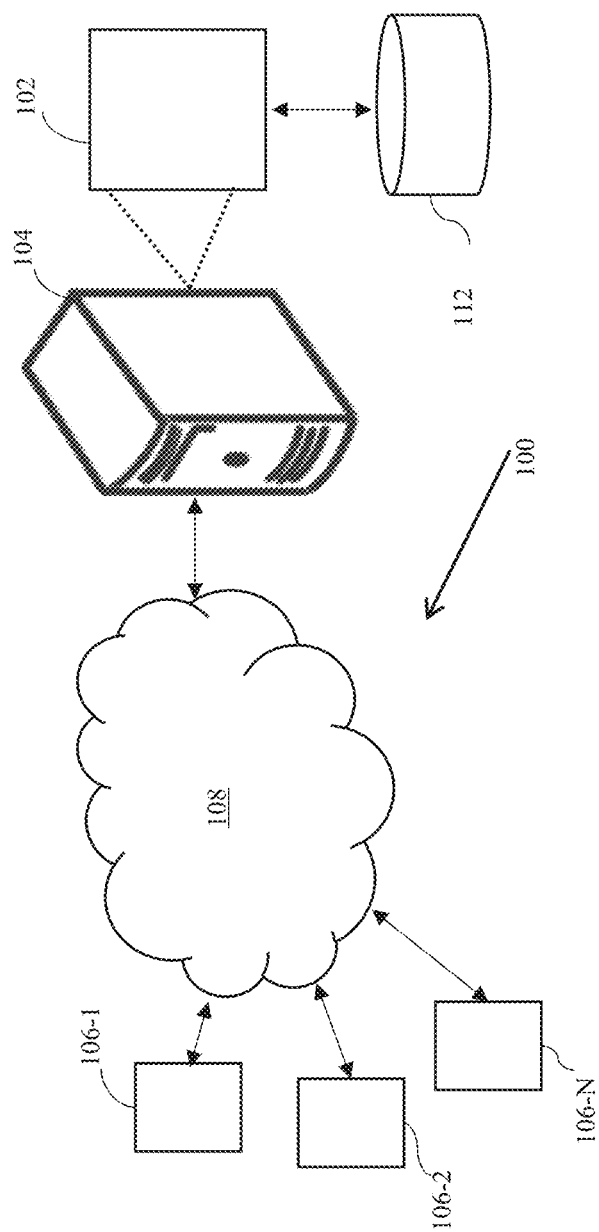
FIG. 1 illustrates an example network implementation of a system for root zone soil moisture estimation for vegetation cover using remote sensing, in accordance with an example embodiment.

Estimating soil moisture under agricultural vegetation in different growth stages is still a challenging task. Due to high penetration and all-weather data acquisition capabilities, few existing solutions have mostly used low-frequency L-band Synthetic Aperture Radar (SAR) satellite data rather than optical data for said estimation. This is due to its higher penetration potential across dense vegetation as compared to the other available band such as C and X. However, a few optical remote sensing-based studies have been carried out that simply analyze the correlation between NDVI and soil moisture under vegetation. The acquisition of L-band satellite data across the Indian region is not as frequent as other SAR satellites such as C-band Sentinel-1. Presently, ALOS-2 is the only active L-band SAR mission hosted by the Japan Aerospace Exploration Agency (JAXA). Over the Indian region, ALOS-2 acquisition frequency is much lower, therefore, it is difficult to develop agriculture monitoring services only using this platform. Moreover, the known systems typically do not consider initial bare surface soil moisture conditions for estimating soil moisture at progressive stages of crop growth i.e. under crop vegetation, thereby leading to improper irrigation of fields.

In light of the aforementioned shortcomings and other known limitations, the disclosed embodiments consider initial moisture content of the soil and estimate soil moisture at different crop growth stages. For example, the disclosed method and system estimating volumetric soil moisture at different stages of crop growth using initial bare surface soil moisture information along with the satellite-derived indexes such as normalized difference vegetation index (NDVI), leaf area index (LAI), relative vegetation index (RVI), and vegetation structure obtained at progressive crop stages. The disclosed system can be further calibrated as per the soil type. Such an approach facilitates in understanding actual moisture condition of the soil and avoid excessive water usage for agricultural irrigation. Soil moisture-based irrigation can be a systematic approach to optimize the demand for irrigation water (and avoiding excessive water usage for agricultural irrigation). Soil moisture-based irrigation can be a systematic approach to optimize the demand for irrigation water.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 1 through 5, where similar reference characters denote corresponding features consistently throughout the figures, there are shown preferred embodiments and these embodiments are described in the context of the following exemplary system and/or method.

FIG. 1 illustrates an example network implementation 100 of a system 102 for root zone soil moisture estimation for vegetation cover using remote sensing, in accordance with an example embodiment. The disclosed system is capable of estimating volumetric soil moisture at different stages of crop growth using initial bare surface soil moisture information along with the satellite-derived indexes such as normalized difference vegetation index (NDVI), leaf area index (LAI), relative vegetation index (RVI), vegetation structure obtained at progressive crop stages.

Although the present disclosure is explained considering that the system 102 is implemented on a server, it may be understood that the system 102 may also be implemented in a variety of computing systems 104, such as a laptop computer, a desktop computer, a notebook, a workstation, a cloud-based computing environment and the like. It will be understood that the system 102 may be accessed through one or more devices 106-1, 106-2 . . . 106-N, collectively referred to as devices 106 hereinafter, or applications residing on the devices 106. Examples of the devices 106 may include, but are not limited to, a portable computer, a personal digital assistant, a handheld device, a smartphone, a tablet computer, a workstation and the like. The devices 106 are communicatively coupled to the system 102 through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a PDA, a smartphone, and a desktop computer. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112.

The network environment 100 supports various connectivity options such as BLUETOOTH®, USB, ZigBee and other cellular services. The network environment enables connection of devices 106 such as Smartphone with the server 104, and accordingly with the database 112 using any communication link including Internet, WAN, MAN, and so on. In an exemplary embodiment, the system 102 is implemented to operate as a stand-alone device. In another embodiment, the system 102 may be implemented to work as a loosely coupled device to a smart computing environment. The components and functionalities of the system 102 are described further in detail with reference to FIGS. 2A-5. An example representation of a method of root zone soil moisture estimation for vegetation cover using remote sensing is described further with reference to FIGS. 2A-2C.

Figure 2A:
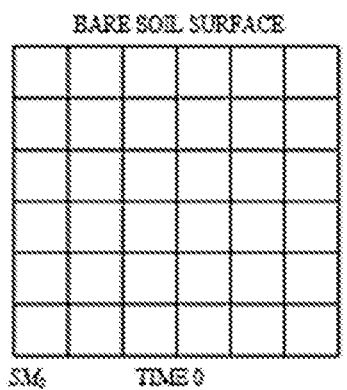
FIG. 2A illustrates a bare soil surface representation in an exemplary a method of root zone soil moisture estimation for vegetation cover using remote sensing in accordance with embodiments of the present disclosure.
Figure 2B:
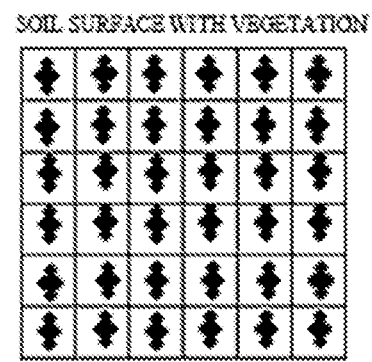
FIG. 2B illustrates a soil surface with vegetation representation in an exemplary a method of root zone soil moisture estimation for vegetation cover using remote sensing in accordance with embodiments of the present disclosure.
Figure 2C:
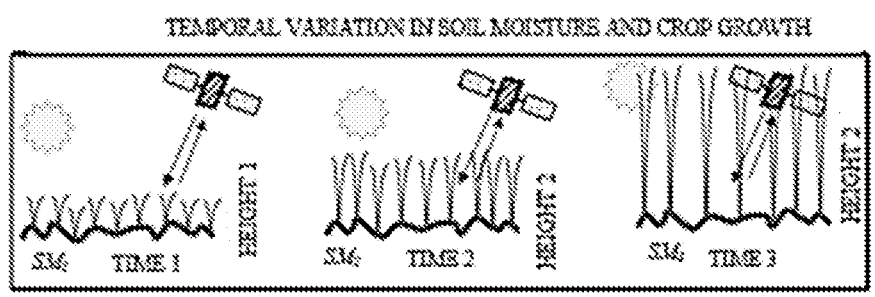
FIG. 2C illustrates a temporal variation in soil moisture and crop growth representation in an exemplary a method of root zone soil moisture estimation for vegetation cover using remote sensing in accordance with embodiments of the present disclosure.

FIGS. 2A-2C illustrates an example representation of a method of root zone soil moisture estimation for vegetation cover using remote sensing in accordance with embodiments of the present disclosure. In particular, FIG. 2A illustrates initial bare surface soil conditions of an agriculture field 202 at time to having soil moisture sm0. Over a period of time, the soil with vegetation cover continues to develop in the progressive stages as illustrated in FIGS. 2B and 2C, respectively. Herein, sm1 is the soil moisture under vegetation height 'Height 1' at a time Time 1'. Similarly, in the case of 'Time 2' and 'Time 3', the soil moisture under vegetation is at height 'Height 2' and 'Height 3' respectively. The entire duration of crop growth can be monitored through remote sensing, using for example, Sentinel-2 satellite data, which can be used to calculate different crop indexes. The overall process flow for under vegetation soil moisture estimation described further with reference to FIG. 3.

FIG. 3 illustrates an example flow chart of a method 300 for root zone soil moisture estimation for vegetation cover using remote sensing, in accordance with an example embodiment of the present disclosure. The method 300 depicted in the flow chart may be executed by a system, for example, the system, 100 of FIG. 1. In an example embodiment, the system 100 may be embodied in a computing device.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 200 are described with help of system 100. However, the operations of the method 200 can be described and/or practiced by using any other system.

At 302, the method 300 includes estimating bare surface soil moisture associated with bare soil in a geographical area. Herein, the geographical area may refer to a field, a farmland, or any other land area which can be utilized for the purpose of growing vegetation. In an embodiment, the bare surface soil moisture may be estimated by applying a soil moisture estimation model to a remote sensing derived data. Herein, the remote sensing derived data may be the data derived from images obtained from a remote sensing device such as a satellite. The satellite may capture images of the geographical area using a technique such a hyperspectral imaging, multispectral imaging and so on. Said images may be preprocessed and the preprocessed images may be utilized as input the disclosed system. Hence, for the brevity of description, the remote sensing derived data (including the preprocessed images) may herein be referred to as remote sensing data. The remote sensing data may be obtained under 'no-vegetation' condition (or bare soil as is shown in FIG. 2A) in the geographical area using a remote sensing technique. In an embodiment, the bare surface soil moisture ($SM_{surface(0)}$) is estimated through empirical or semi-empirical relationship (as illustrated in Equation 1 below) using the remote sensing derived data. In an embodiment, the remote sensing derived data may include radar backscatter ($\sigma_0$).

$$SM_{surface(0)} = m^*(\sigma_0) + c \qquad (1)$$

where, m is the gradient and c is intercept.

At 304, the method 300 includes estimating, at a plurality of time-instants, vegetation surface soil moisture associated with the soil in the geographical area under vegetation cover on the soil. The plurality of time instants refers to multiple subsequent time instants during the growth of the vegetation in the geographical area. The vegetation surface soil moisture ($SM_{surface(t)}$) at the plurality of time instants can be computed based on the bare soil moisture, a soil parameter, a weather parameter, a crop parameter, one or more time-series satellite derived remote sensing parameters. The one or more time-series satellite derived remote sensing parameters derived based on optical sensing data obtained at the plurality of time instants. The optical satellite (e.g., Landsat, Sentinel-2 etc.) derived indexes at a time instant t includes, for example, Normalized Difference Vegetation Index (NDVI), Radar Vegetation Index (RVI), Leaf Area Index (LAI), vegetation structure, and so on, at that time t. The estimation of vegetation surface soil moisture under vegetation cover at various time instances (or crop seasons) is computed using empirical/semi-empirical relationship given in Equation 2:

$$SM_{surface(t)} = \beta_0 + \beta_1 \cdot X_1 + \beta_2 \cdot X_2 + \beta_3 \cdot X_3 + \beta_4 \cdot X_4 + \beta_5 \cdot X_5 + \sigma \quad (2)$$

where, $SM_{surface(t)}$=soil moisture at time t;
$\beta_0$=intercept;
$\beta_1, \beta_2, \beta_3, \beta_4$=regression coefficients;
X1=$SM_{surface(0)}$, bare soil moisture at time 0;
X2=$sm_p$, soil parameter;
X3=$w_p$, weather parameter
X4=$c_p$, Crop parameter;
X5=$Index_p$, index value (e.g. Normalized Difference Vegetation Index
(NDVI), Enhanced Vegetation Index (EVI)) at time t;
$\sigma$=residual Herein, the parameter X5 may be estimated using band information obtained from satellite data (e.g. Sentinel-1 or Landsat-7/8 satellite data). For example, NDVI may be estimated by using following equation:

$$NDVI = \frac{NIRband - REDband}{NIRband + REDband} \quad (3)$$

The EVI may be determined by using the band information obtained from the satellite data by using the following equation:

$$EVI = \frac{2.5 * (NIRband - REDband)}{(NIR + 6 * REDband - 7.5 * BLUEband) + 1} \quad (4)$$

At 306, the method includes estimating a point-based root zone soil moisture ($Sm_{root\ zone(p)}$) using a using soil water balance model. The soil water balance model computes root zone water balance on a periodic basis based on water stored in the root zone at periodic intervals, and precipitation, irrigation, drainage and evapotranspiration amount of water during the periodic intervals. The point-based root-zone soil moisture ($SM_{root\ zone(p)}$) using water balance model is estimated using the following equation:

$$\Delta S = P + I - (D + ET) \quad (5)$$

where, $\Delta S$ is the change in root-zone soil-moisture storage,
P is the amount of precipitation,
I is the amount of irrigation water applied,
D is the amount of downward drainage out of the root zone, and
ET is Evapotranspiration.

The root zone water balance is calculated on a daily basis. The following equation can be used for daily water balance computation:

$$S_i = S_{i-1} + P_i + I_i - (D_i + ET_i) \quad (6)$$

where, $S_i$ and $S_{i-1}$ are amounts of water stored in the root zone at the end of day i and day i−1, respectively. $P_i$, $D_i$, and $ET_i$ represent precipitation, irrigation, drainage, and evapotranspiration amounts on day i.

Figure 4:
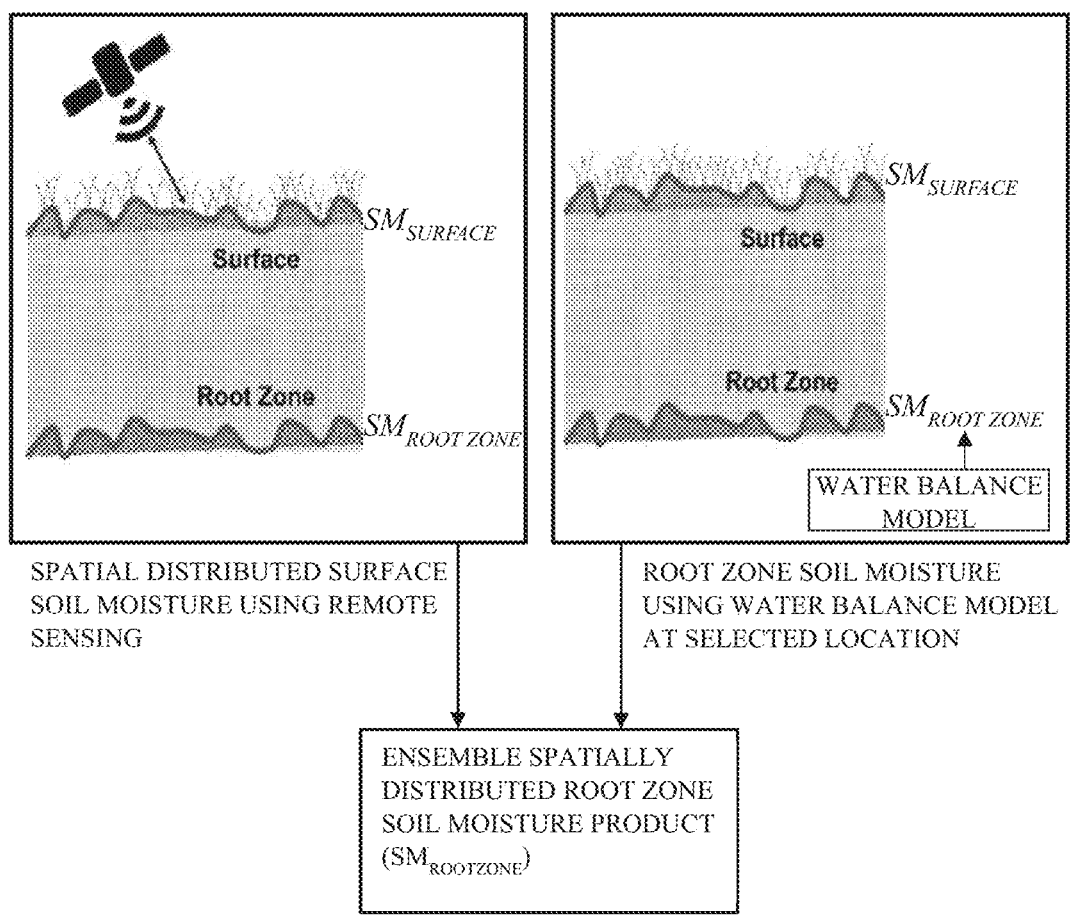
FIG. 4 illustrates an exemplary representation of estimating an ensemble of vegetation soil moisture and point based root zone soil moisture according to some embodiments of the present disclosure.

The vegetation surface soil moisture ($SM_{surface(t)}$) (estimated at 304) and the point based root zone soil moisture ($SM_{root\ zone(p)}$) (estimated at 306) are utilized for determining spatially distributed root zone soil moisture ($SM_{root\ zone(SD)}$) at the geographical location at 308, as illustrated in FIG. 4. Herein, $SM_{root\ zone(SD)}$ is a function of $SM_{surface(t)}$ and $SM_{root\ zone(p)}$. The spatially distributed root zone soil moisture (SMroot zone(SD)) may be estimated using the ensemble of vegetation soil moisture (SMsurface (t)) and point based root zone soil moisture (SMroot zone (p)). Estimating the spatially distributed root zone soil moisture ($SM_{root\ zone(SD)}$) will be described in detail with reference to an example scenario.

Figure 5:
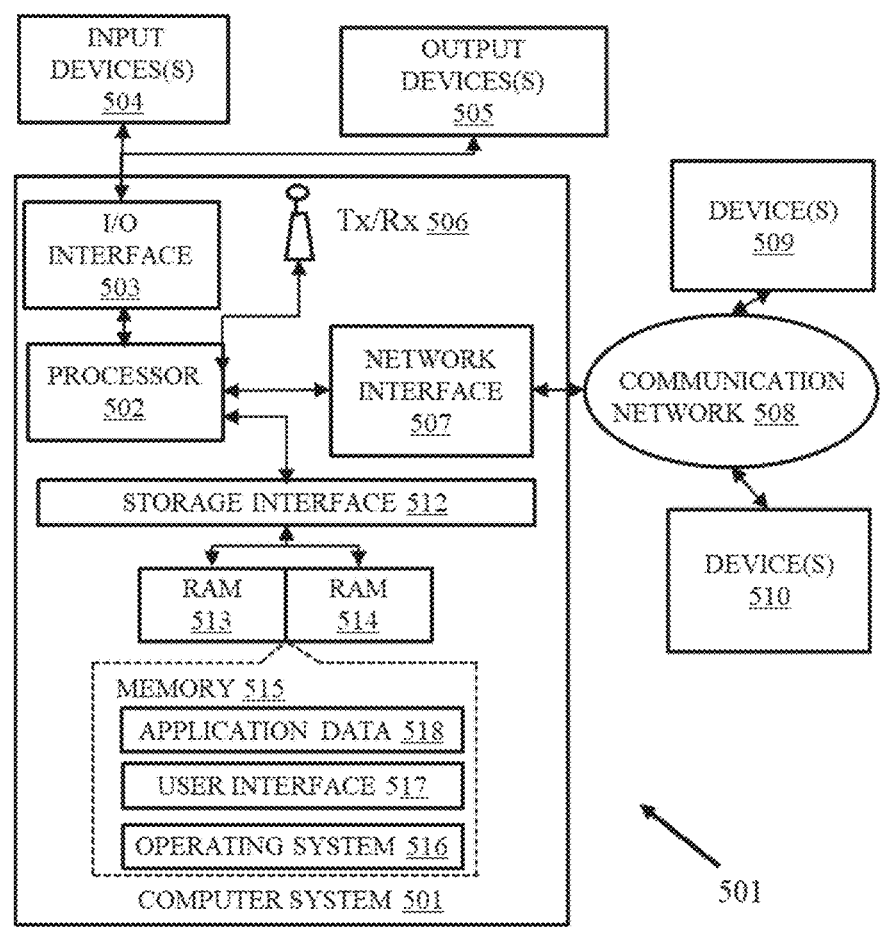
FIG. 5 is a block diagram of an exemplary computer system for implementing embodiments consistent with the present disclosure.

FIG. 5 is a block diagram of an exemplary computer system 501 for implementing embodiments consistent with the present disclosure. The computer system 501 may be implemented in alone or in combination of components of the system 102 (FIG. 1). Variations of computer system 501 may be used for implementing the devices included in this disclosure. Computer system 501 may comprise a central processing unit ("CPU" or "hardware processor") 502. The hardware processor 502 may comprise at least one data processor for executing program components for executing user- or system-generated requests. The processor may include specialized processing units such as integrated system (bus) controllers, memory management control units, floating point units, graphics processing units, digital signal processing units, etc. The processor may include a microprocessor, such as AMD Athlon™, Duron™ or Opteron™, ARM's application, embedded or secure processors, IBM PowerPC™, Intel's Core, Itanium™, Xeon™, Celeron™ or other line of processors, etc. The processor 502 may be implemented using mainframe, distributed processor, multi-core, parallel, grid, or other architectures. Some embodiments may utilize embedded technologies like application specific integrated circuits (ASICs), digital signal processors (DSPs), Field Programmable Gate Arrays (FPGAs), etc. The processor 502 may be a multi-core multi-threaded processor.

Processor 502 may be disposed in communication with one or more input/output (I/O) devices via I/O interface 503. The I/O interface 503 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11 a/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 503, the computer system 501 may communicate with one or more I/O devices. For example, the input device 504 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc.

Output device 505 may be a printer, fax machine, video display (e.g., cathode ray tube (CRT), liquid crystal display (LCD), light-emitting diode (LED), plasma, or the like), audio speaker, etc. In some embodiments, a transceiver 306 may be disposed in connection with the processor 502. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 502 may be disposed in communication with a communication network 508 via a network interface 507. The network interface 507 may communicate with the communication network 508. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 308 may include, without limitation, a direct interconnection, local area network (LAN), wide area network (WAN), wireless network (e.g., using Wireless Application Protocol), the Internet, etc. Using the network interface 507 and the communication network 508, the computer system 501 may communicate with devices 509 and 510. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 501 may itself embody one or more of these devices.

In some embodiments, the processor 502 may be disposed in communication with one or more memory devices (e.g., RAM 513, ROM 514, etc.) via a storage interface 512. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc. Variations of memory devices may be used for implementing, for example, any databases utilized in this disclosure.

The memory devices may store a collection of programs or database components, including, without limitation, an operating system 516, user interface application 517, user/application data 518 (e.g., any data variables or data records discussed in this disclosure), etc. The operating system 516 may facilitate resource management and operation of the computer system 501. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 517 may facilitate display, execution, interaction, manipulation, or operation of program components through textual or graphical facilities. For example, user interfaces may provide computer interaction interface elements on a display system operatively connected to the computer system 501, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, computer system 501 may store user/application data 318, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, structured text file (e.g., XML), table, or as hand-oriented databases (e.g., using HandStore, Poet, Zope, etc.). Such databases may be consolidated or distributed, sometimes among various computer systems discussed above. It is to be understood that the structure and operation of any computer or database component may be combined, consolidated, or distributed in any working combination.

Additionally, in some embodiments, (the server, messaging and instructions transmitted or received may emanate from hardware, including operating system, and program code (i.e., application code) residing in a cloud implementation. Further, it should be noted that one or more of the systems and methods provided herein may be suitable for cloud-based implementation. For example, in some embodiments, some or all of the data used in the disclosed methods may be sourced from or stored on any cloud computing platform.

Figure 6A:
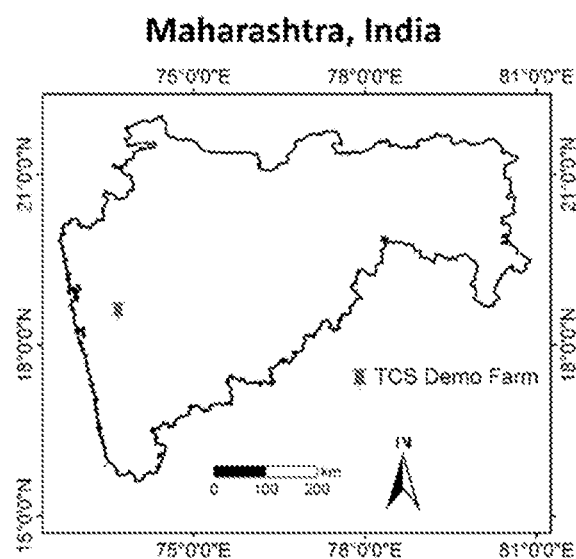
FIGS. 6A and 6B illustrate an example scenario for root zone soil moisture estimation for vegetation cover using remote sensing, according to some embodiments of the present disclosure.
Figure 6B:
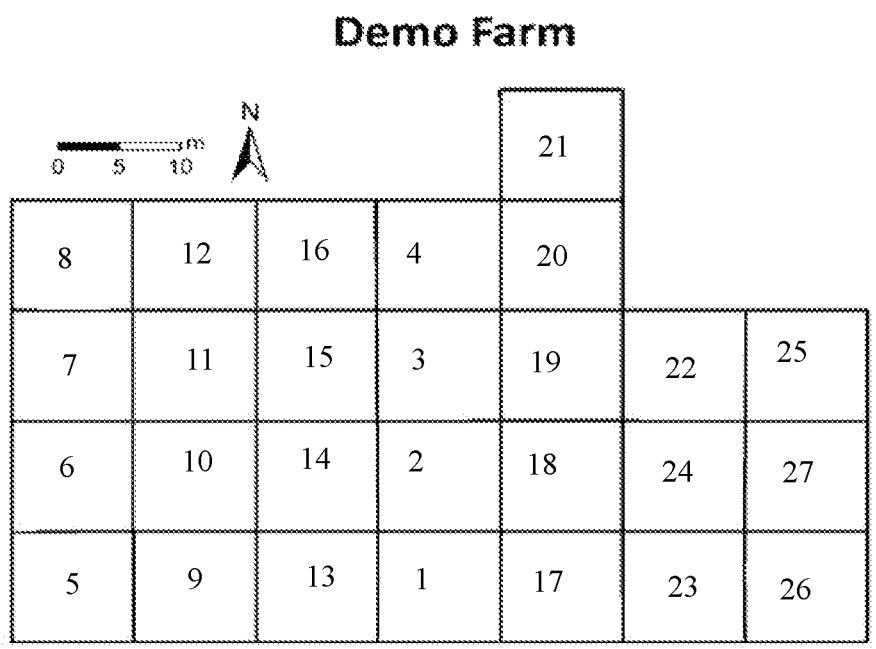

For demonstrating the end-to-end processing of the disclosed embodiments, an experiment scenario is presented. In an experiment scenario, the processing was performed over a demo farm located in Pune (India), as illustrated in FIGS. 6A and 6B. Particularly, in FIG. 6B, the demo farm is divided into 27 pixels (given number 1 to 27), each 10×10 m size. Initially, for estimating bare surface soil moisture (SMsurface(0)) from Equation 1 (described above), the spatially distributed radar backscatter (σ0) was derived by pre-processing the Sentinel-1 raw satellite data. The representative values of σ0 for the study location are given below as matrix (A). The σ0 values varies from region to region based on soil type, texture etc. In matrix (A), "nan" values are assigned to the pixels that fall outside the farm boundary. Similar rule was followed for other matrixes. The estimated $SM_{surface(0)}$ is given in matrix (B).

$$\sigma_0 = \begin{bmatrix} nan & nan & nan & nan & -11 & nan & nan \\ -11 & -11 & -10 & -10 & -12 & nan & nan \\ -11 & -11 & -11 & -10 & -12 & -10 & -12 \\ -11 & -11 & -10 & -10 & -10 & -10 & -12 \\ -11 & -11 & -11 & -10 & -12 & -10 & -10 \end{bmatrix} \quad (A)$$

$$SM_{surface(0)} = \begin{bmatrix} nan & nan & nan & nan & 15 & nan & nan \\ 15 & 20 & 25 & 20 & 15 & nan & nan \\ 20 & 20 & 15 & 20 & 15 & 20 & 20 \\ 15 & 15 & 25 & 25 & 20 & 15 & 15 \\ 20 & 20 & 25 & 20 & 25 & 15 & 20 \end{bmatrix} \quad (B)$$

Subsequently, vegetation surface soil moisture under vegetation cover (i.e. $SM_{surface(t)}$) at various time instances (or crop seasons) was computed using empirical/semi-empirical relationship given in Equation 2 (described above). This equation utilizes $SM_{surface(0)}$, indices such as NDVI (Equation 3) or EVI (Equation 4) values (refer matrix (C) and matrix (D)) derived by using the band information obtained from the satellite data and other region-specific information of soil (e.g. type/texture), weather (e.g. temperature/humidity), and crop (e.g. type). The estimated representative values of $SM_{surface(t)}$ is given in matrix (E).

$$NDVI = \begin{bmatrix} nan & nan & nan & nan & 0.5 & nan & nan \\ 0.4 & 0.6 & 0.5 & 0.5 & 0.5 & nan & nan \\ 0.4 & 0.6 & 0.5 & 0.5 & 0.5 & 0.4 & 0.6 \\ 0.5 & 0.6 & 0.5 & 0.5 & 0.5 & 0.5 & 0.5 \\ 0.5 & 0.6 & 0.5 & 0.5 & 0.5 & 0.5 & 0.5 \end{bmatrix} \quad (C)$$

$$EVI = \begin{bmatrix} nan & nan & nan & nan & 0.6 & nan & nan \\ 0.5 & 0.6 & 0.6 & 0.5 & 0.6 & nan & nan \\ 0.6 & 0.6 & 0.5 & 0.5 & 0.5 & 0.6 & 0.6 \\ 0.6 & 0.5 & 0.5 & 0.6 & 0.6 & 0.6 & 0.5 \\ 0.6 & 0.5 & 0.6 & 0.6 & 0.5 & 0.6 & 0.6 \end{bmatrix} \quad (D)$$

$$SM_{surface(t)} = \begin{bmatrix} nan & nan & nan & nan & 15 & nan & nan \\ 25 & 20 & 25 & 25 & 25 & nan & nan \\ 23 & 25 & 25 & 20 & 20 & 20 & 23 \\ 20 & 20 & 25 & 25 & 25 & 25 & 25 \\ 25 & 20 & 25 & 25 & 25 & 20 & 20 \end{bmatrix} \quad (E)$$

Subsequently, point-based root-zone soil moisture ($SM_{root\ zone(p)}$) at certain locations were estimated using water balance model given in Equation 5 and 6.

The estimated $SM_{root\ zone(p)}$ is given below as matrix (F).

$$SM_{root\ zone(p)} = \begin{bmatrix} nan & nan & nan & nan & 15 & nan & nan \\ 25 & nan & nan & nan & nan & nan & nan \\ nan & nan & 25 & nan & nan & nan & 23 \\ nan & nan & nan & nan & 25 & nan & nan \\ nan & 20 & nan & 25 & 25 & nan & nan \end{bmatrix} \quad (F)$$

Finally, the spatially distributed root zone soil moisture ($SM_{root\ zone(SD)}$) was estimated using the ensemble of vegetation soil moisture ($SM_{surface(t)}$) and point based root zone soil moisture ($SM_{root\ zone(p)}$) at the particular geographical location. Herein, $SM_{root\ zone(SD)}$ is a function of $SM_{surface(t)}$ and $SM_{root\ zone(p)}$. Representative values of $SM_{root\ zone(SD)}$ is given below in matrix (G).

$$SM_{root\ zone(SD)} = \begin{bmatrix} nan & nan & nan & nan & 15 & nan & nan \\ 25 & 25 & 18 & 20 & 20 & nan & nan \\ 22 & 22 & 25 & 25 & 20 & 20 & 23 \\ 25 & 20 & 20 & 22 & 25 & 22 & 22 \\ 22 & 22 & 22 & 20 & 20 & 20 & 20 \end{bmatrix} \quad (G)$$

Herein, it will be understood that the disclosed scenario is presented as an exemplary case for the purpose of clarity and should not be construed as limiting to the presented embodiments. Further, it will be understood that under different geography conditions, the results of aforementioned computations shall vary.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments describe method and system for root zone soil moisture estimation for vegetation cover using remote sensing. In traditional methods, it is not possible to estimate root zone soil moisture estimation using only satellite data. Additionally, methods to estimate soil moisture under vegetation cover based on bare surface soil moisture and vegetation parameters is not available. Moreover, the soil water balance technique is point based and has limited scalability. The disclosed method and system overcome aforementioned limitation of the traditional systems by estimating an ensemble of soil moisture under vegetation cover and root zone soil moisture using process based soil water balance for spatial estimation of root zone soil moisture.

In an embodiment, bare surface soil moisture (i.e. sm0 at time t0) is extracted from the empirical or semi-empirical models/algorithms that uses radar backscattering parameter (in vertical-vertical and vertical-horizontal polarizations) derived from C-band SAR data (such as Sentinel-1) as an input. A function is developed where soil moisture at any time t (i.e. Time 1, Time 2, Time 3) can be estimated using sm0 and indexes such as NDVI, RVI, LIA, vegetation structure and so on derived from optical satellite (e.g. Landsat, Sentinel-2 etc.) at that particular time t. Further, for accuracy assessment, observed and measured soil moisture will be compared. The disclosed system can be further calibrated as per the soil type/texture/roughness parameter(s), which may be given as an input to the developed function. Such soil parameter(s) can be measured in the field or estimated using some remote sensing techniques employed with empirical/semi-empirical/physical models.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for root zone soil moisture estimation under vegetation using remote sensing, the method comprising:
    estimating bare surface soil moisture associated with bare soil in a geographical area by applying a soil moisture estimation model to a remote sensing derived data, via one or more hardware processors, wherein the remote sensing derived data obtained under no-vegetation condition in the geographical area using a remote sensing technique;
    estimating, at a plurality of time-instants, the vegetation surface soil moisture associated with the soil in the geographical area under vegetation cover on the soil, via the one or more hardware processors, wherein the vegetation surface soil moisture at the plurality of time instants computed based on the bare soil moisture, a soil parameter, a weather parameter, a crop parameter, one or more time-series satellite derived remote sensing parameters, wherein the one or more time-series satellite derived remote sensing parameters derived based on optical sensing data obtained at the plurality of time instants;
    estimating, via the one or more hardware processors, a point-based root zone soil moisture using a soil water balance model, wherein the soil water balance model computes root zone water balance on a periodic basis based on water stored in the root zone at periodic intervals, and precipitation, irrigation, drainage and evapotranspiration amount of water during the periodic intervals; and
    determining, via the one or more hardware processors, spatially distributed root zone soil moisture at the geographical location using the vegetation surface soil moisture and the point-based root zone soil moisture.

2. The processor implemented method of claim 1, wherein the bare surface soil moisture is estimated based on the soil moisture estimation model of the following equation:

$$SM_{surface(0)}=m*(\sigma_0)+c$$

where, m is the gradient, c is intercept and $\sigma_0$ is backscatter.

3. The processor implemented method of claim 1, wherein the one or more time-series satellite derived remote sensing parameters comprises Normalized Difference Vegetation Index (NDVI), Enhanced Vegetation Index (EVI), Vegetation Index (RVI), and Leaf Area Index (LAI).

4. The processor implemented method of claim 3, wherein the NDVI is determined by using band information obtained from the satellite data by using the following equation:

$$NDVI = \frac{NIRband - band}{NIRband + band}.$$

5. The processor implemented method of claim 3, wherein the EVI is determined by using band information obtained from the satellite data by using the following equation:

$$EVI = \frac{2.5*(NIRband - band)}{(NIR + 6*band - 7.5*band) + 1}.$$

6. The processor implemented method of claim 1, wherein the vegetation surface soil moisture is estimated based on the following equation:

$$SM_{surface(t)}=\beta0+\beta1\cdot X1+\beta2\cdot X2+\beta3\cdot X3+\beta4\cdot X4+\beta5\cdot X5+\sigma$$

wherein
$SM_{surface(t)}$=soil moisture at time t;
$\beta_0$=intercept;
$\beta_1, \beta_2, \beta_3, \beta_4$=regression coefficients;
X1=$SM_{surface(0)}$, bare soil moisture at time 0;
X2=$sm_p$, soil parameter;
X3=$w_p$, weather parameter
X4=$c_p$, Crop parameter;
X5=$Index_t$, index value (e.g. Normalized Difference Vegetation Index
(NDVI), Enhanced Vegetation Index (EVI)) at time t;
$\sigma$=residual.

7. The processor implemented method of claim 1, wherein the point based root-zone soil moisture ($SM_{root\ zone(p)}$) using water balance model is estimated using the following equation:

$$\Delta S=P+I-(D+ET)$$

$\Delta S$ is the change in root-zone soil-moisture storage,
P is the amount of precipitation,
I is the amount of irrigation water applied, D is the amount of downward drainage out of the root zone, and ET is Evapotranspiration.

8. A system for root zone soil moisture estimation under vegetation using remote sensing, comprising:
- a memory storing instructions; and
- one or more hardware processors coupled to the memory, wherein the
- one or more hardware processors are configured by the instructions to:
  - estimate bare surface soil moisture associated with bare soil in a geographical area by applying a soil moisture estimation model to a remote sensing derived data, the remote sensing derived data obtained under no-vegetation condition in the geographical area using a remote sensing technique;
  - estimate, at a plurality of time-instants, vegetation surface soil moisture associated with the soil in the geographical area under vegetation cover on the soil, the vegetation surface soil moisture at the plurality of time instants computed based on the bare soil moisture, a soil parameter, a weather parameter, a crop parameter, one or more time-series satellite derived remote sensing parameters, wherein the one or more time-series satellite derived remote sensing parameters derived based on optical sensing data obtained at the plurality of time instants;
  - estimate a point-based root zone soil moisture using a using soil water balance model, wherein the soil water balance model computes root zone water balance on a periodic basis based on water stored in the root zone at periodic intervals, and precipitation, irrigation, drainage and evapotranspiration amount of water during the periodic intervals; and
  - determine spatially distributed root zone soil moisture at the geographical location using the vegetation surface soil moisture and point based root zone soil moisture.

9. The system of claim 8, wherein the bare surface soil moisture is estimated based on the soil moisture estimation model of the following equation:

$$SM_{surface(0)} = m*(\sigma^0) + c$$

where, m is the gradient, c is intercept and $\sigma_0$ is backscatter.

10. The system of claim 8, wherein the one or more time-series satellite derived remote sensing parameters comprises Normalized Difference Vegetation Index (NDVI), Enhanced Vegetation Index (EVI), Vegetation Index (RVI), and Leaf Area Index (LAI).

11. The system of claim 10, wherein the NDVI is determined by using band information obtained from the satellite data by using the following equation:

$$NDVI = \frac{NIRband - band}{NIRband + band}.$$

12. The system of claim 10, wherein the EVI is determined by using band information obtained from the satellite data by using the following equation:

$$EVI = \frac{2.5 * (NIRband - band)}{(NIR + 6 * band - 7.5 * band) + 1}.$$

13. The system of claim 8, wherein the vegetation surface soil moisture is estimated based on the following equation:

$$SM_{surface(t)} = \beta 0 + \beta 1 \cdot X1 + \beta 2 \cdot X2 + \beta 3 \cdot X3 + \beta 4 \cdot X4 + \beta 5 \cdot X5 + \sigma$$

wherein, $SM_{surface(t)}$=soil moisture at time t;

$\beta_0$=intercept;

$\beta_1, \beta_2, \beta_3, \beta_4$=regression coefficients;

X1=$SM_{surface(0)}$, bare soil moisture at time 0;

X2=$sm_p$, soil parameter;

X3=$w_p$, weather parameter

X4=$c_p$, Crop parameter;

X5=$Index_t$, index value (e.g. Normalized Difference Vegetation Index (NDVI), Enhanced Vegetation Index (EVI)) at time t;

$\sigma$=residual.

14. The system of claim 8, wherein the point based root-zone soil moisture ($SM_{root\ zone(p)}$) using water balance model is estimated using the following equation:

$$\Delta S = P + I - (D + ET)$$

$\Delta S$ is the change in root-zone soil-moisture storage,

P is the amount of precipitation,

I is the amount of irrigation water applied,

D is the amount of downward drainage out of the root zone, and

ET is Evapotranspiration.

15. One or more non-transitory machine-readable information storage mediums comprising one or more instructions which when executed by one or more hardware processors cause:
- estimating bare surface soil moisture associated with bare soil in a geographical area by applying a soil moisture estimation model to a remote sensing derived data, via one or more hardware processors, wherein the remote sensing derived data obtained under no-vegetation condition in the geographical area using a remote sensing technique;
- estimating, at a plurality of time-instants, the vegetation surface soil moisture associated with the soil in the geographical area under vegetation cover on the soil, via the one or more hardware processors, wherein the vegetation surface soil moisture at the plurality of time instants computed based on the bare soil moisture, a soil parameter, a weather parameter, a crop parameter, one or more time-series satellite derived remote sensing parameters, wherein the one or more time-series satellite derived remote sensing parameters derived based on optical sensing data obtained at the plurality of time instants;
- estimating, via the one or more hardware processors, a point-based root zone soil moisture using a soil water balance model, wherein the soil water balance model computes root zone water balance on a periodic basis based on water stored in the root zone at periodic intervals, and precipitation, irrigation, drainage and evapotranspiration amount of water during the periodic intervals; and
- determining, via the one or more hardware processors, spatially distributed root zone soil moisture at the geographical location using the vegetation surface soil moisture and the point-based root zone soil moisture.

* * * * *